(12) United States Patent
Lord, III et al.

(10) Patent No.: US 11,101,473 B2
(45) Date of Patent: Aug. 24, 2021

(54) SYSTEM AND METHOD FOR MONITORING AMMONIUM BISULFIDE

(71) Applicants: Charles John Lord, III, Bartlesville, OK (US); John Stephen Newland, Bartlesville, OK (US)

(72) Inventors: Charles John Lord, III, Bartlesville, OK (US); John Stephen Newland, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 13/804,530

(22) Filed: Mar. 14, 2013

(65) Prior Publication Data

US 2013/0271149 A1    Oct. 17, 2013

Related U.S. Application Data

(60) Provisional application No. 61/623,814, filed on Apr. 13, 2012.

(51) Int. Cl.
| | | |
|---|---|---|
| *G01N 27/416* | (2006.01) | |
| *H01M 8/0297* | (2016.01) | |
| *G01N 27/08* | (2006.01) | |
| *G01N 33/18* | (2006.01) | |
| *H01M 8/10* | (2016.01) | |
| *H01M 8/026* | (2016.01) | |

(52) U.S. Cl.
CPC .......... *H01M 8/0297* (2013.01); *G01N 27/08* (2013.01); *G01N 33/1893* (2013.01); *H01M 8/10* (2013.01); *H01M 8/026* (2013.01)

(58) Field of Classification Search
CPC ..... G01N 27/023; G01N 24/085; G01N 27/08
See application file for complete search history.

(56) References Cited

U.S. PATENT DOCUMENTS

| | | | |
|---|---|---|---|
| 3,674,672 A | | 7/1972 | Whitesell |
| 4,266,188 A | * | 5/1981 | Thompson ............ G01R 27/22 |
| | | | 324/606 |
| 5,157,332 A | | 10/1992 | Reese |
| 5,545,303 A | | 8/1996 | Schasfoort et al. |
| 5,656,151 A | | 8/1997 | McLaughlin et al. |
| 7,405,572 B2 | * | 7/2008 | Quackenbush et al. ...... 324/445 |
| 7,691,329 B2 | | 4/2010 | Potyrailo et al. |
| 2004/0265174 A1 | * | 12/2004 | Mehus .................... D06F 34/22 |
| | | | 422/67 |
| 2005/0127919 A1 | * | 6/2005 | Feng et al. .................... 324/439 |

(Continued)

OTHER PUBLICATIONS

Web page for Applied Analytics, Inc.: "Hydrogen Sulfide Analyzer—H2S Analyzer", "NOVA-II: NOVA-II Spectrometer", The Measurement Principle: UV-VIS Spectroscopy, 3 pages.

Sridhar Srinivasan, Vishal Lagad, Honeywell International, Inc., "Evaluation of Prediction Tool for Sour Water Corrosion Quantification and Management in Refineries", Paper No. 09337, NACE Corrosion 2009 Conference & Expo, 17 pages.

(Continued)

*Primary Examiner* — Son T Le
*Assistant Examiner* — Adam S Clarke
(74) *Attorney, Agent, or Firm* — Phillips 66 Copmany

(57) ABSTRACT

Systems and methods relate to measuring ammonium bisulfide concentration in a fluid sample. The system includes an electrolytic conductivity cell, a temperature sensor and an analyzer. Logic of the analyzer determines the ammonium bisulfide concentration based on signals received from the conductivity cell and the temperature sensor that are coupled to monitor the fluid.

7 Claims, 12 Drawing Sheets

(56) References Cited

U.S. PATENT DOCUMENTS

| | | | | |
|---|---|---|---|---|
| 2006/0217895 | A1* | 9/2006 | Iwawaki | G01N 17/00 702/30 |
| 2010/0023275 | A1* | 1/2010 | Trygstad | G01N 21/359 702/25 |
| 2010/0292944 | A1* | 11/2010 | Howell | G01N 27/08 702/65 |
| 2010/0294021 | A1* | 11/2010 | Makino | G01N 25/18 73/25.03 |
| 2011/0001490 | A1* | 1/2011 | Eberheim | G01N 27/023 324/654 |
| 2012/0091049 | A1* | 4/2012 | West et al. | 210/149 |
| 2012/0326711 | A1* | 12/2012 | Roper | G01N 27/025 324/252 |

OTHER PUBLICATIONS

Presentation by Vishal Lagad, Sridhar Srinivasan, Honeywell, Prediction of NH4H5 Corrosion in Sour Water Systems, Predict-SW 3.0, Failure Prevention, Risk Mitigation, Optimized Material Selection, 40 pages.

Vishal V. Lagad, Michael S. Cayard, Sridhar Srinivasan, "Prediction and Assessment of Rich Amine Corrosion Under Simulated Refinery Conditions", Paper No. 10183, NACE Corrosion 2010 Conference & Expo, 14 pages.

PCT Notification of Transmittal of the International Search Report and the Written Opinion of the International Searching Authority, or the Declaration, International Application No. PCT/US2013/031356, International Filing Date: Mar. 14, 2013, 17 pages.

\* cited by examiner

SYSTEM AND METHOD FOR MONITORING AMMONIUM BISULFIDE

CROSS-REFERENCE TO RELATED APPLICATIONS

This application is a non-provisional application which claims benefit under 35 USC § 119(e) to U.S. Provisional Application Ser. No. 61/623,814 filed Apr. 13, 2012, entitled "Monitoring Ammonium Bisulfide," which is incorporated herein in its entirety.

STATEMENT REGARDING FEDERALLY SPONSORED RESEARCH OR DEVELOPMENT

None.

FIELD OF THE INVENTION

The invention relates to an online system and method for measuring ammonium bisulfide, and, in particular, to a method for measuring ammonium bisulfide in a fluid stream using an electrolytic conductivity device.

BACKGROUND OF THE INVENTION

Refineries hydrotreat middle distillates and intermediate feedstocks to remove nitrogen and sulfur compounds before forming finished petroleum products. The effluent sour water from this hydroprocessing contains ammonia ($NH_3$) and hydrogen sulfide ($H_2S$). As the effluent cools, an ammonium bisulfide ($NH_4HS$) salt forms in the sour water from reaction of the hydrogen sulfide and ammonia as follows:

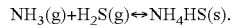

$$NH_3(g) + H_2S(g) \leftrightarrow NH_4HS(s).$$

The ammonium bisulfide causes accelerated corrosion and maintenance problems for given metallurgy in the refinery depending on concentrations. Resulting corrosion problems and failures can result in personal injury, costly equipment damage and lost production. Predicting corrosion caused by the sour water relies on accurate monitoring of the ammonium bisulfide concentration. Without knowing or lacking confidence in the ammonium bisulfide concentration, operators make unnecessary feed rate cuts and use excessive wash water to avoid corrosion issues.

Because there is typically more sulfur than nitrogen in the feedstocks, the concentration of the ammonium bisulfide is often estimated by the amount of ammonia present in the "grab" samples of the effluent. These grab samples are analyzed in a refinery laboratory using alkalinity titration method. However, these lab-analyzed samples only provide intermittent data and pose a safety risk to sample collectors due to potential exposure to the hydrogen sulfide degassing. Another approach attempts to estimate the ammonium bisulfide concentration based on refinery operating conditions but generates results with over 50% uncertainty.

Therefore, there is the need for an accurate online system and method for measuring ammonium bisulfide concentration.

SUMMARY OF THE INVENTION

The present invention provides an online system and method for monitoring ammonium bisulfide, and, in particular, a method for monitoring ammonium bisulfide in a fluid stream using an electrolytic conductivity device.

In some embodiments, a system for measuring ammonium bisulfide concentration in a fluid stream includes a conductivity cell, a temperature sensor and an analyzer. The conductivity cell measures electrolytic conductivity of the fluid stream that flows through the cell. Logic of the analyzer determines the ammonium bisulfide concentration based on signals received from the conductivity cell and the temperature sensor coupled to measure temperature of the fluid stream.

According to some embodiments, a method of measuring ammonium bisulfide concentration in a fluid stream includes measuring electrolytic conductivity of the fluid stream. The method further includes measuring temperature of the fluid stream. Determination of the ammonium bisulfide concentration relies on the temperature and the conductivity that are measured.

For some embodiments, a computer-readable storage-medium contains a program for measuring ammonium bisulfide concentration in a fluid stream. The program, when executed, performs a method that includes receiving a first signal indicative of electrolytic conductivity for the fluid stream and a second signal indicative of temperature of the fluid stream. In addition, the method performed by the program includes determining the ammonium bisulfide concentration based on the first and second signals.

These and other objects, features, and advantages will become apparent as reference is made to the following detailed description, preferred embodiments, and examples, given for the purpose of disclosure, and taken in conjunction with the accompanying drawings and appended claims.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Figure 1:
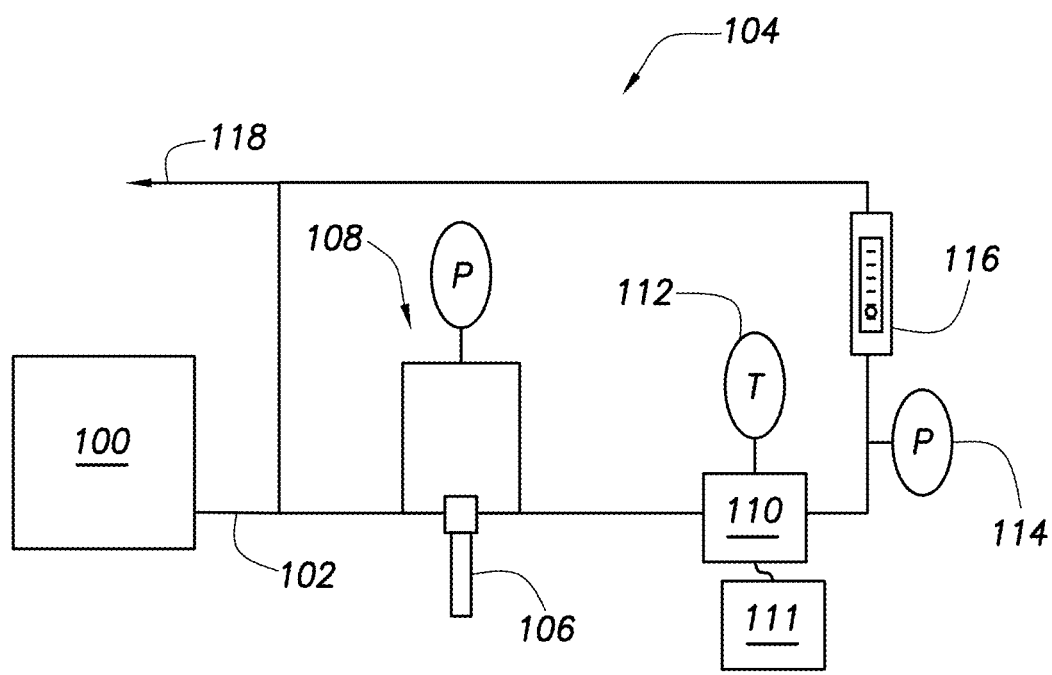
FIG. 1 illustrates a schematic diagram of an ammonium bisulfide analyzer system according to an embodiment of the present invention.

The following detailed description of various embodiments of the present invention references the accompanying drawings, which illustrate specific embodiments in which the invention can be practiced. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. Therefore, the scope of the present invention is defined only by the appended claims, along with the full scope of equivalents to which such claims are entitled.

Embodiments of the invention relate to a system and method for measuring ammonium bisulfide concentration in a fluid stream, such as an aqueous liquid stream. The system includes an electrolytic conductivity cell 110, a temperature sensor 112 and an analyzer 111. In an embodiment, the system may also include a pressure sensor 114. Logic of the analyzer 111 determines the ammonium bisulfide concentration based on signals received from the conductivity cell 110, the temperature sensor 112 and, optionally, pressure sensor 114 that are coupled to monitor the fluid stream 102.

FIG. 1 illustrates a schematic diagram of an ammonium bisulfide analyzer system according to an embodiment of the present invention. In operation, a source 100, such as any combination of various refinery units including hydrotreaters, hydrocrackers, sour water strippers and fluid catalytic crackers, outputs a sour aqueous liquid stream 102. At least part of the stream 102 enters an analyzer flow loop 104. If only a portion of the stream 102 is diverted into the flow loop 104, a sufficient pressure differential between entry and exit of the flow loop 104 may ensure flow of the stream 102 through the flow loop 104. In an embodiment, the conductivity cell 110, temperature sensor 112 and, optionally, pressure sensor 114 are disposed along an output of sour water at a refinery such that the fluid stream 102 contains at least part of the sour water.

For some embodiments, the flow loop 104 includes a filter 106 for removing particulates from the stream 102 that may influence conductivity of the stream 102. Examples of the filter 106 include porous media based elements that prevent passage of the particulates based on size exclusion. A suitable filter is available from Hatfield & Company, Inc. A differential pressure gauge 108 coupled to sense upstream and downstream of the filter 106 may provide an indication of when the filter 106 becomes plugged and requires changing. Depending on the amount of contaminants introduced from the source 100, the stream 102 may however not require any filtering before passing through a conductivity cell 110 disposed along the flow loop 104. In an embodiment, the conductivity cell 110, the temperature sensor 112 and, optionally, the pressure sensor 114 are disposed along an analyzer flow loop 104 coupled in fluid communication with flow of hydrotreater sour water 100 to produce the fluid stream 102 within the analyzer loop 104.

The conductivity cell 110 represents any device capable of measuring electrolytic conductivity of the fluid stream 102. In some embodiments, the conductivity cell 110 senses the conductivity inductively using electromagnetic coils without direct contact with the stream 102 passing through an internal conduit of the conductivity cell 110. In other words, the inductive conductivity cell 110 is isolated from direct contact with the stream 102. This lack of direct-contact by the conductivity cell 110 with the stream 102 avoids potential fouling problems, which could adversely impact readings. For example, a suitable non-contact conductivity cell 110 is available from Rosemount Analytical, Inc. ("Rosemount"). The conductivity cell 110 known as a flow-through cell type may further pass the stream 102 from a bottom to a top of the conductivity cell 110 so that any bubbles in the stream 102 float to the top in order to limit influence on the readings.

Figure 17:
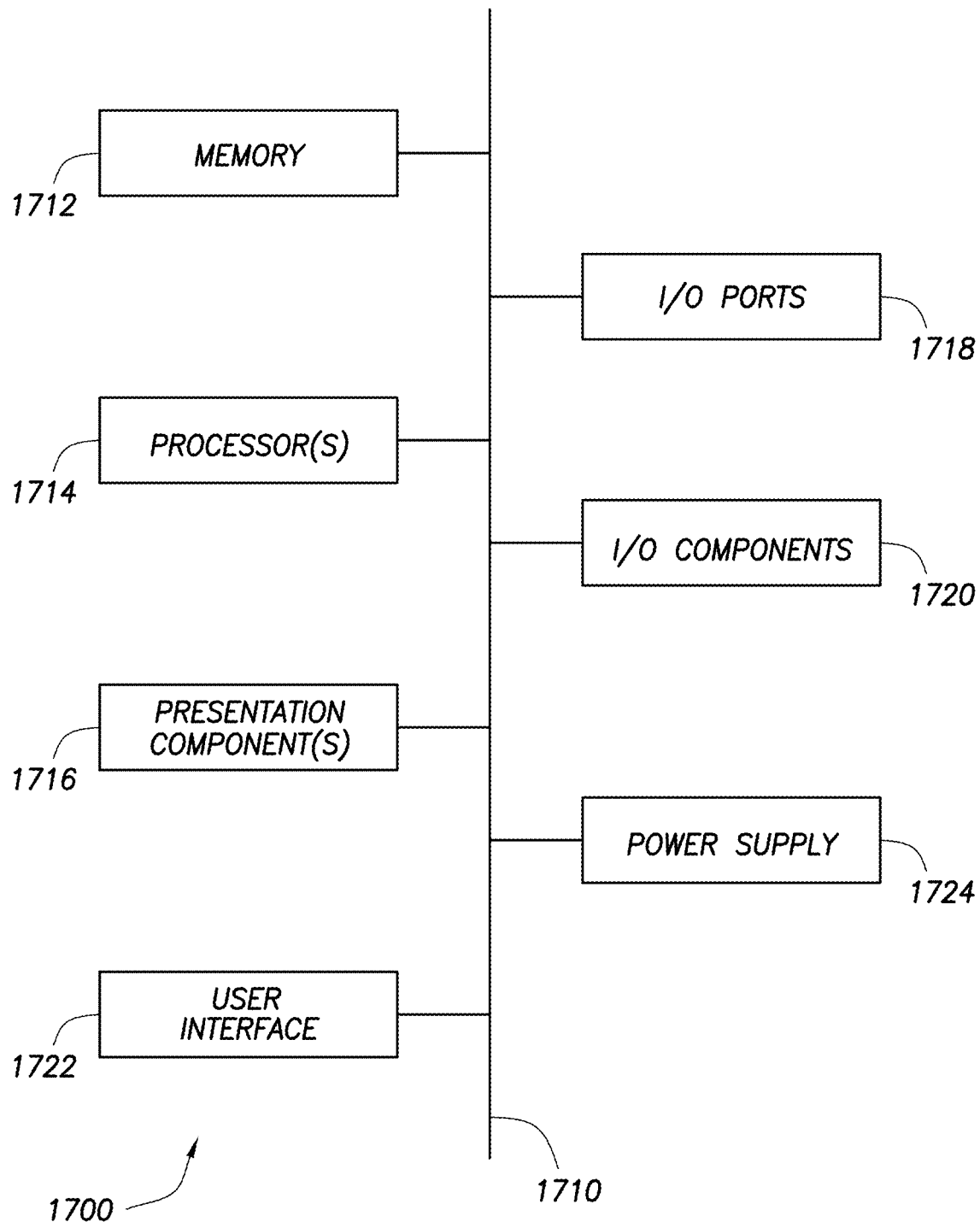
FIG. 17 illustrates a schematic diagram of a computing device for an ammonium bisulfide analyzer according to an embodiment of the present invention.

FIG. 17 illustrates a schematic diagram of a computing device for an ammonium bisulfide analyzer system according to an embodiment of the present invention. Referring to the drawings in general, and initially to FIGS. 1 and 17 in particular, an exemplary operating environment for implementing embodiments of the present invention is shown and designated generally as a computing device 1700 for the analyzer 111. The computing device 1700 is but one example of a suitable computing environment and is not intended to suggest any limitation as to the scope of use or functionality of the invention. Neither should the computing device 1700 be interpreted as having any dependency or requirement relating to any one or combination of components illustrated. For example, a suitable computing device 1700 is available from Rosemount that is designed to be compatible with a suitable conductivity cell 110 also available from Rosemount, as discussed above.

Embodiments of the invention may be described in the general context of computer code or machine-executable instructions stored as program modules or objects and executable by one or more computing devices, such as a laptop, server, mobile device, tablet, etc. Generally, program modules including routines, programs, objects, components, data structures, etc., refer to code that perform particular tasks or implement particular abstract data types. Embodiments of the invention may be practiced in a variety of system configurations, including handheld devices, consumer electronics, general-purpose computers, more specialty computing devices, and the like. Embodiments of the invention may also be practiced in distributed computing environments where tasks may be performed by remote-processing devices that may be linked through a communications network.

With continued reference to FIG. 17, the computing device 1700 of the analyzer 100 includes a bus 1710 that directly or indirectly couples the following devices: memory 1712, one or more processors 1714, one or more presentation components 1716, one or more input/output (I/O) ports 1718, I/O components 1720, a user interface 1722 and an illustrative power supply 1724. The bus 1710 represents what may be one or more busses (such as an address bus, data bus, or combination thereof). Although the various blocks of FIG. 17 are shown with lines for the sake of clarity, in reality, delineating various components is not so clear, and metaphorically, the lines would more accurately be fuzzy. For example, one may consider a presentation component such as a display device to be an I/O component. Additionally, many processors have memory. The inventors recognize that such is the nature of the art, and reiterate that the diagram of FIG. 17 is merely illustrative of an exemplary computing device that can be used in connection with one or more embodiments of the present invention. Further, a distinction is not made between such categories as "workstation," "server," "laptop," "mobile device," etc., as all are contemplated within the scope of FIG. 17 and reference to "computing device."

The computing device 1700 of the analyzer 100 typically includes a variety of computer-readable media. Computer-readable media can be any available media that can be accessed by computing device 1700 and includes both volatile and nonvolatile media, removable and non-removable media. By way of example, and not limitation, computer-readable media may comprise computer-storage media and communication media. The computer-storage media includes volatile and nonvolatile, removable and non-removable media implemented in any method or technology for storage of information such as computer-readable instructions, data structures, program modules or other data. Computer-storage media includes, but is not limited to, Random Access Memory (RAM), Read Only Memory (ROM), Electronically Erasable Programmable Read Only Memory (EEPROM), flash memory or other memory technology, CD-ROM, digital versatile disks (DVD) or other holographic memory, magnetic cassettes, magnetic tape, magnetic disk storage or other magnetic storage devices, or any other medium that can be used to encode desired information and which can be accessed by the computing device 1700.

The memory 1712 includes computer-storage media in the form of volatile and/or nonvolatile memory. The memory 1712 may be removable, non-removable, or a combination thereof. Suitable hardware devices include solid-state memory, hard drives, optical-disc drives, etc. The computing device 1700 of the analyzer 100 includes one or more processors 1714 that read data from various entities such as the memory 1712 or the I/O components 1720.

Figure 18:
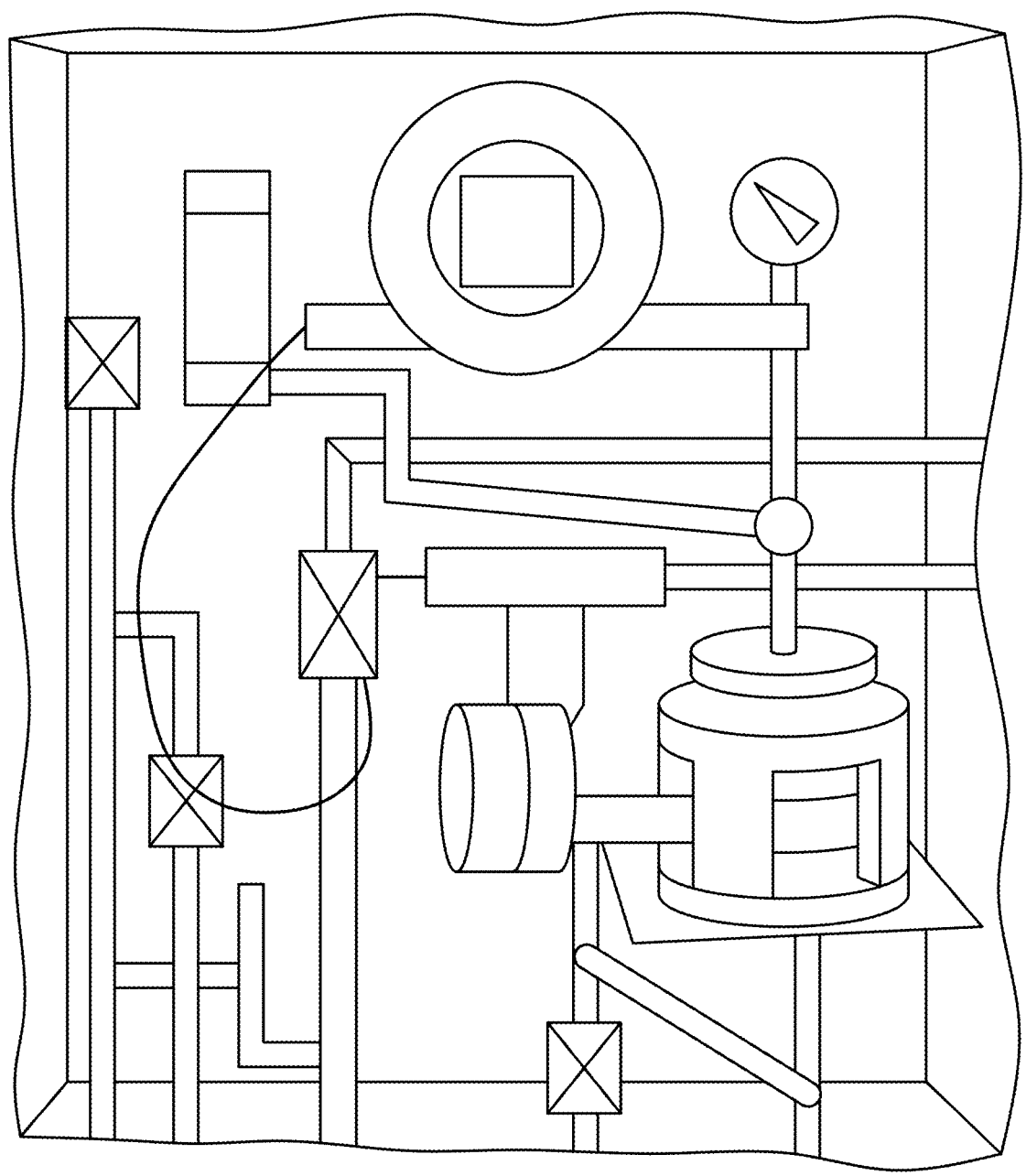
FIG. 18 illustrates a diagram of a prototype ammonium bisulfide analyzer according to an embodiment of the present invention, showing an exemplary electrolytic conductivity cell and computing device from Rosemount Analytical, Inc.

The presentation component(s) 1716 present data indications to a user or other device. In an embodiment, the computing device 1700 outputs present data indications including ammonium bisulfide concentration, temperature, pressure and/or the like to a presentation component 1716. See e.g., FIG. 18. Suitable presentation components 1716 include a display device, speaker, printing component, vibrating component, and the like.

The user interface 1722 allows the user to input/output information to/from the computing device 1700. Suitable user interfaces 1722 include keyboards, key pads, touch pads, graphical touch screens, and the like. For example, the user may input an ammonium bisulfide calibration algorithm or curve into the computing device 1700 or output an ammonium bisulfide concentration to the presentation component 1716 such as a display. In some embodiments, the user interface 1722 may be combined with the presentation component 1716, such as a display and a graphical touch screen. In some embodiments, the user interface may be a portable hand-held device. Suitable user interfaces including portable hand-held devices are available from Rosemount. The use of such devices is well-known in the art.

The one or more I/O ports 1718 allow the computing device 1700 to be logically coupled to other devices including a conductivity cell 110, the temperature sensor 112, the optional pressure sensor 114, and other I/O components 1720, some of which may be built in. Examples of other I/O components 1720 include a printer, scanner, wireless device, and the like.

In operation, the conductivity cell 110 sends a first signal indicative of the electrolytic conductivity to computing device 1700 of analyzer 111 via a first I/O port 1718a. In some embodiments, the computing device 1700 of analyzer 111 also receives a second signal from the temperature sensor 112 via a second I/O port 1718b. The temperature sensor 112 represents any device capable of measuring temperature of the fluid stream 102. Examples of temperature sensors 112 include thermocouples, resistance temperature detectors (RTD) and the like. A suitable RTD is available from Omega Engineering. The temperature sensor 112 enables determining temperature of the stream 102 when passing through the conductivity cell 110 and, thus, the temperature sensor 112 may be disposed at or near the conductivity cell 110. For example, in a factory configuration, the Rosemount conductivity cell 110 utilizes the temperature sensor 112 located directly in contact with a process connection flange. Due to significant thermal mass of the conductivity cell 110, the temperature sensor 112 measures the flange temperature—not the stream temperature. See FIG. 16. As can be seen from FIG. 16, due to the thermal mass of the conductivity cell 110, the flange temperature lags behind the stream temperature when the stream temperature changes. These errors in temperature measurement resulted in about 4% error in the calculated conductivity of the stream. Id.

Figure 16:
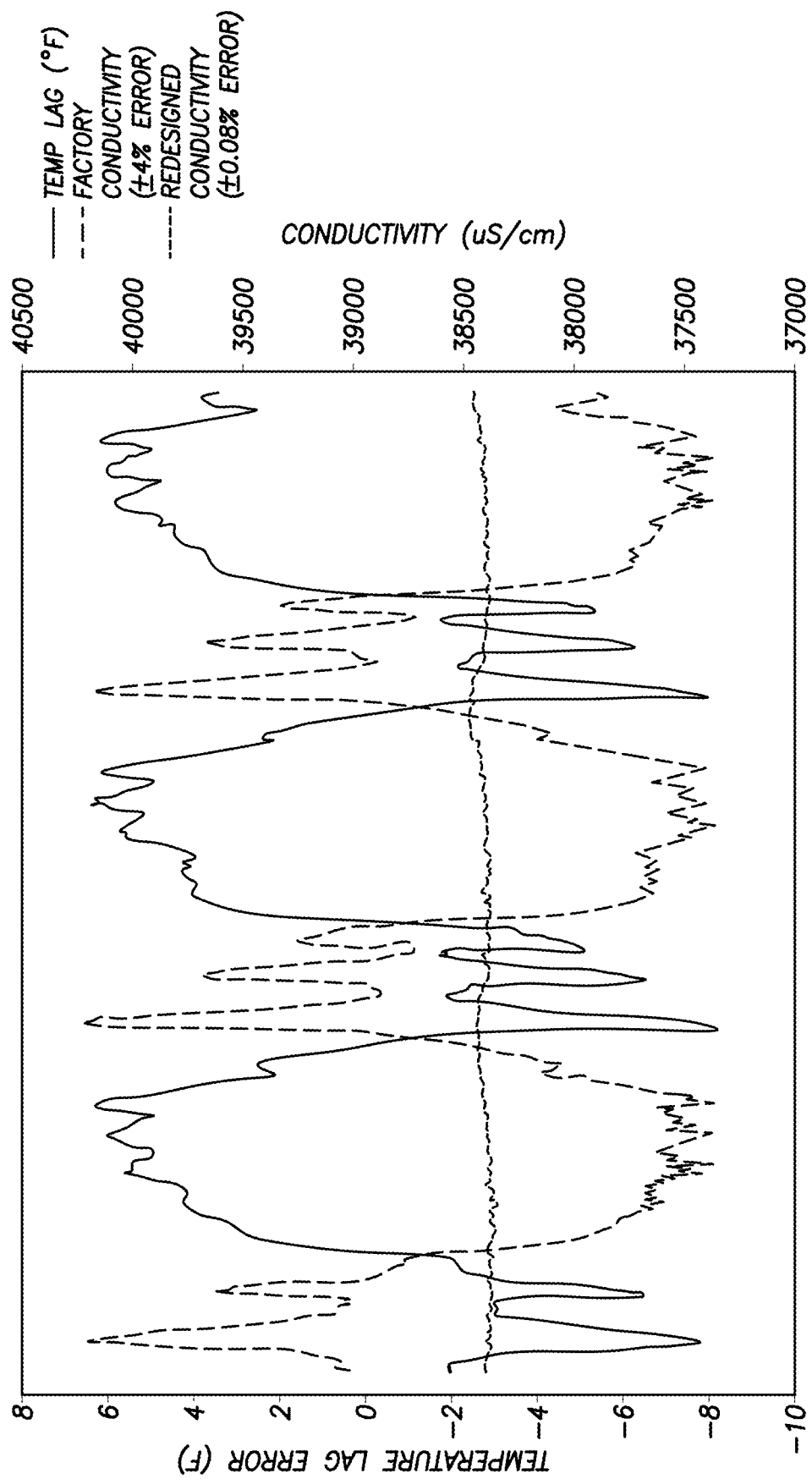
FIG. 16 illustrates a chart of time versus temperature lag error (° F.), showing reduction of conductivity error to 0.08% by moving temperature sensor directly into fluid stream.

Because electrolytic conductivity varies significantly as a function of temperature (i.e., about 2% per ° C.), any temperature compensation should be based upon an accurate temperature measurement of the stream 102. To avoid this thermal transfer delay, some embodiments utilize the temperature sensor 112 located directly in contact with the fluid stream 102. See e.g., FIG. 16. In other words, the temperature sensor 112 may be inserted directly into the stream 102. For example, the temperature sensor 112 in the Rosemount conductivity cell 110 was relocated from direct-contact with the flange to direct-contact with the stream 102. See e.g., FIG. 18. As can be seen in FIG. 16, inserting the temperature sensor 112 directly into the stream 102 improves the accuracy by about a factor of fifty. With these more accurate temperature measurements, the error in the calculated conductivity was significantly reduced to about 0.08%. Id.

For some embodiments, the temperature sensor 112 operates as part of a temperature-regulating device that controls temperature of the stream 102 such that the stream temperature remains constant when passing through the conductivity cell 110 and a constant compensation for temperature can be applied in determination of the ammonium bisulfide concentration.

The analyzer 111 includes logic for determining the ammonium bisulfide concentration based on the first, second and, optionally, third signals received respectively from the conductivity cell 110, the temperature sensor 112 and optionally, the pressure sensor 114. In particular, the conductivity of the stream 102 varies as a function of the ammonium bisulfide concentration with possible compensation for temperature and pressure depending on steadiness of operating conditions for the system. The stream 102 may consist of, or consist essentially of, water and the ammonium bisulfide in solution. Only one salt dominates the stream 102 and is the ammonium bisulfide. The ammonium bisulfide concentration thus provides a controlling constituent of the stream 102 that influences changes in the conductivity, thereby eliminating need for further detection selectivity.

The logic of the analyzer 111 may correlate the measured conductivity, temperature and, optionally, pressure of the stream 102 to an ammonium bisulfide calibration algorithm or curve in order to determine the ammonium bisulfide concentration. In some embodiments, the analyzer 111 outputs the ammonium bisulfide concentration to a presentation component 1716 onsite with the conductivity cell 110 and/or to a remote presentation component 1716, such as a display in a control room or offsite monitoring location. The conductivity cell 110, temperature sensor 112, optionally, pressure sensor 114 or the analyzer 111 may include a cellular modem or wireless device for this output of the ammonium bisulfide concentration to the remote location from the conductivity cell 110. In an embodiment, the presentation component 1716 may show present data indications including ammonium bisulfide concentration as weight percent (wt %) ammonium bisulfide in the stream 102 temperature of the stream 102 in degree Fahrenheit (° F.), and, optionally, pressure of the stream 102 in pounds per square inch gauge (psig). See e.g., FIG. 18.

For some embodiments, theoretical calculations enable defining an ammonium bisulfide calibration algorithm or curve, as discussed further below. This calibration modeling approach avoids use of the ammonium bisulfide for calibration. The theoretical calculations may include several, such as 1000 or more, calculated values for the conductivity over potential operating temperatures, such as about 60 to about 140° F. (i.e., about 15 to about 60° C.), and a potential ammonium bisulfide concentration range, such as about 0 to about 50 wt %. See FIGS. 3-7. These calculated values showed near linear conductivity changes over the concentration range and enabled deriving the algorithm or curve for a concentration-conductivity function with a temperature compensation factor. Id.

In some embodiments, the analyzer 111 operates at temperatures above a freezing point of the stream 102 and up to a maximum temperature where thermal decomposition of the ammonium bisulfide generates non-linear conductivity responses across the concentration range. See FIGS. 3-7; see also FIGS. 8-12. At temperatures above the threshold temperature, the calculated values showed non-linear conductivity changes over the concentration range and precluded deriving an ammonium bisulfide algorithm or curve for the concentration-conductivity function with only the temperature compensation factor. Id. If the stream 102 is not cooled enough from just passing through a length of conduit exposed to ambient air from the source 100 before reaching the conductivity cell 110, optional heat exchangers may provide desired temperature reduction.

Further, in some embodiments, the analyzer 111 operates at pressures between about 30 to 260 psig (i.e., about 200 to about 1750 kilopascal) or an upper limit defined by component pressure ratings. This pressure range also provides a linear response and corresponds with typical cycles as sour water accumulates and discharges from the source 100. See e.g., FIGS. 3-7. Under such desired operating conditions, the pressure of the stream 102 provides limited influence on the conductivity. Id. Some embodiments include the pressure sensor 114, which can provide assurance that the pressure is in an acceptable range for accurate results without further compensation or provide input for additional compensation in the ammonium bisulfide algorithm or curve to determine the ammonium bisulfide concentration. The pressure sensor 114 represents any device capable of measuring pressure of the fluid stream 102. In these embodiments, the computing device 1700 receives a third signal from the pressure sensor 114 via a third I/O port 1718c, as discussed above.

In some embodiments, a flow meter 116 disposed along the flow loop 104 confirms that the stream 102 is flowing through the conductivity cell 110 since the system can provide real-time online measurements. The flow meter 114 represents any device capable of measuring flow rate of the fluid stream 102. The ammonium bisulfide concentration would fail to be updated over time in the absence of the stream 102 moving through the flow loop 104. If flow stops or slows below a threshold value, the computing device 1700 of analyzer 111 may thus indicate an error or otherwise tag the ammonium bisulfide concentration that is determined and output. In these embodiments, the computing device 1700 receives a fourth signal from the flow meter 116 via a fourth I/O port 1718d.

In some embodiments, the analyzer 111 outputs the ammonium bisulfide concentration at specified intervals, such as every second or minute. Continuous automatic monitoring by the analyzer 111 permits integration of the analyzer 111 with other process controls that can adjust levels of the ammonium bisulfide in the stream 102 based on the ammonium bisulfide concentration that is determined. For some embodiments, the analyzer 111 may output an alarm signal if the ammonium bisulfide concentration exceeds a maximum value as determined by metallurgy being employed.

The stream 102 exits the flow loop 104 and is sent as a waste output 118 for treatment or reuse. The waste output 118 may include any of the stream 102 not diverted through the flow loop 104. In some embodiments, at least about 7 psig (i.e., about 50 kilopascal) pressure differential between where part of the stream 102 enters the flow loop 104 and combines back to form the waste output 118 maintains desired flow.

Figure 2:
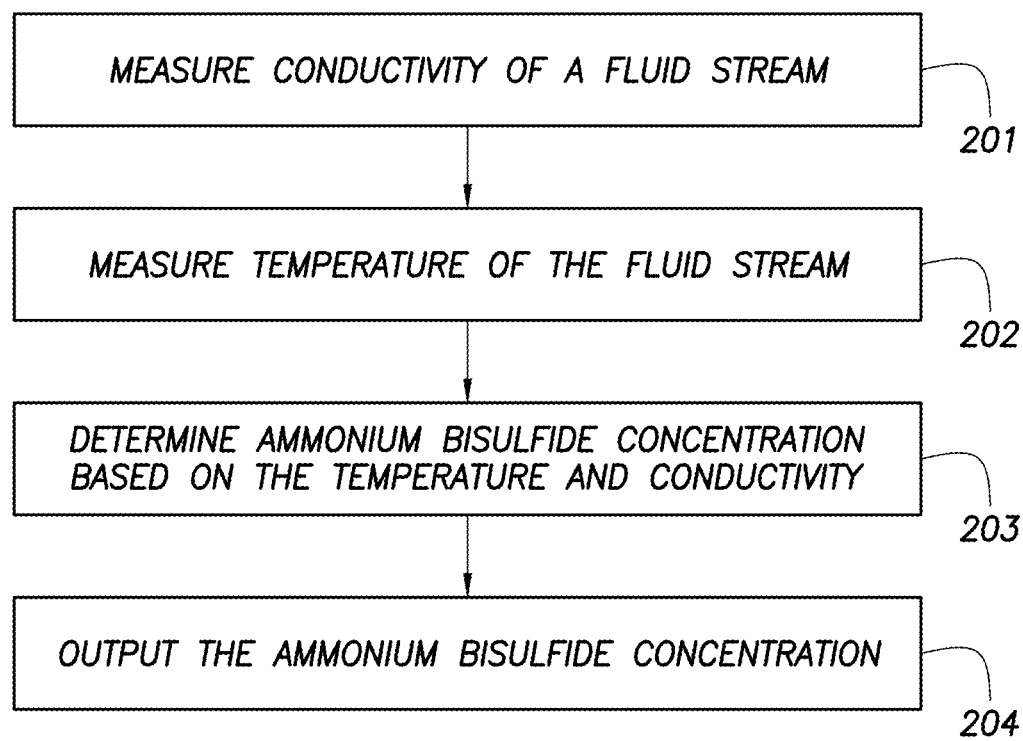
FIG. 2 illustrates a flow chart for a method of measuring ammonium bisulfide concentration in a fluid stream.
Figure 3:
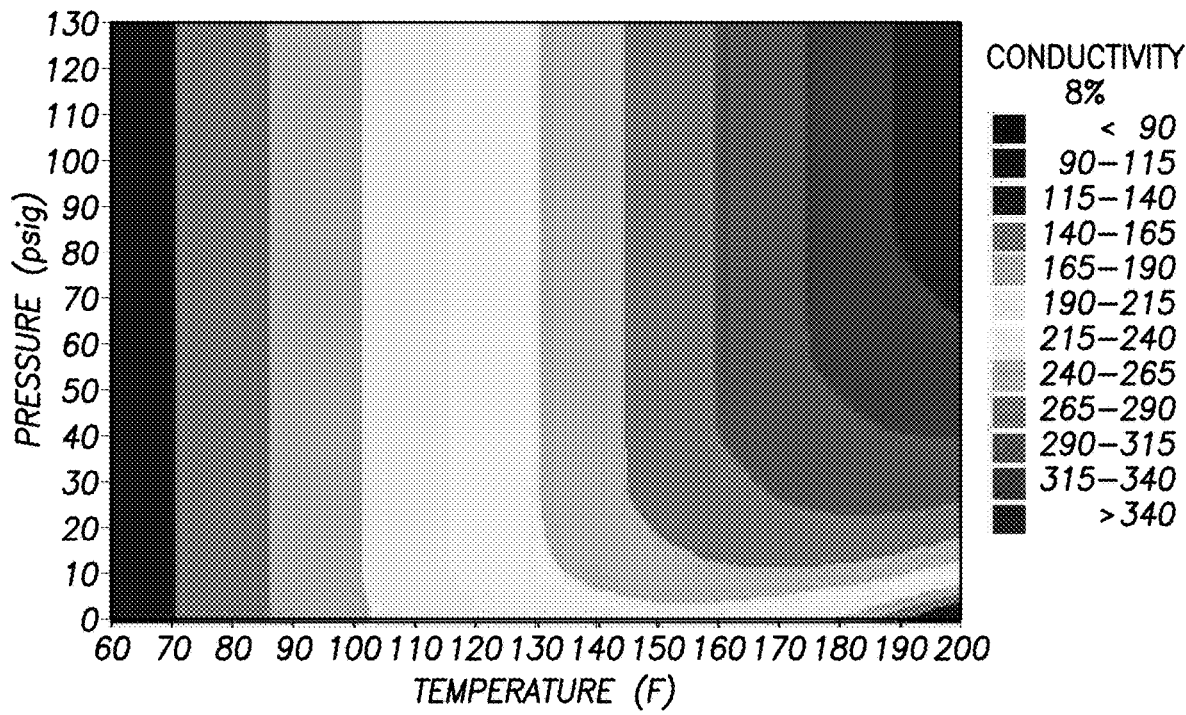
FIG. 3 illustrates a chart of temperature (° F.) versus pressure (psig) for electrolytic conductivity (mS/cm) of 8 wt % ammonium bisulfide.
Figure 4:
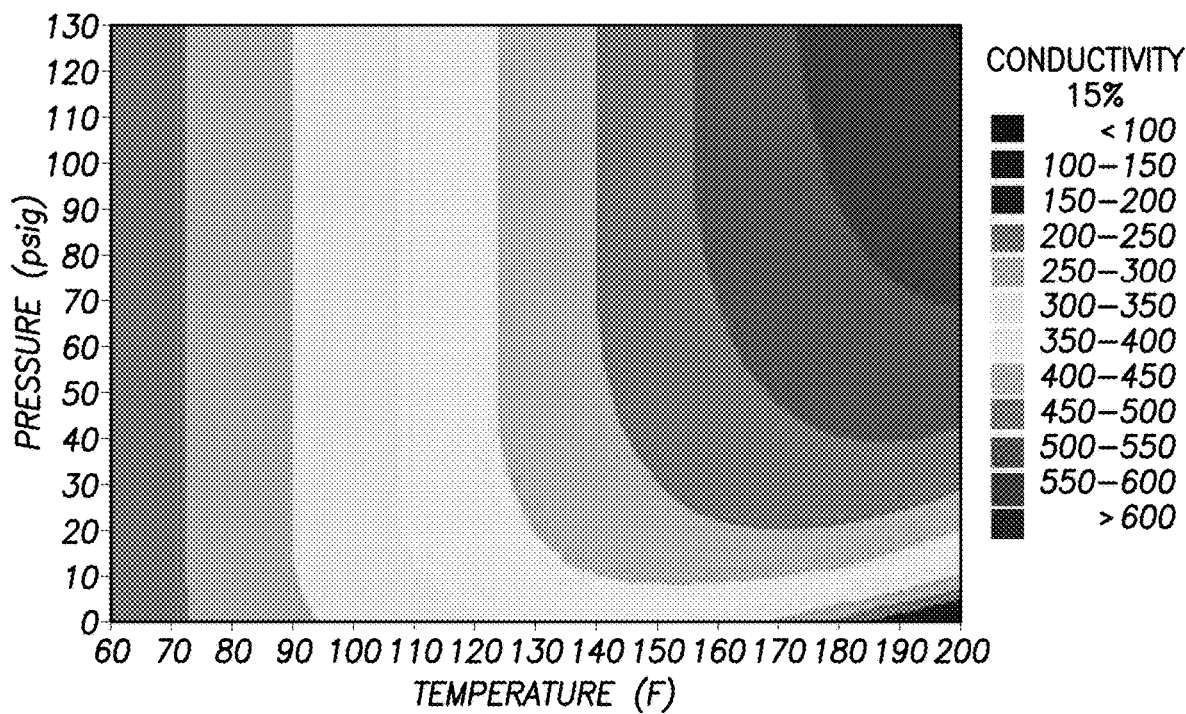
FIG. 4 illustrates a chart of temperature (° F.) versus pressure (psig) for electrolytic conductivity (mS/cm) of 15 wt % ammonium bisulfide.
Figure 5:
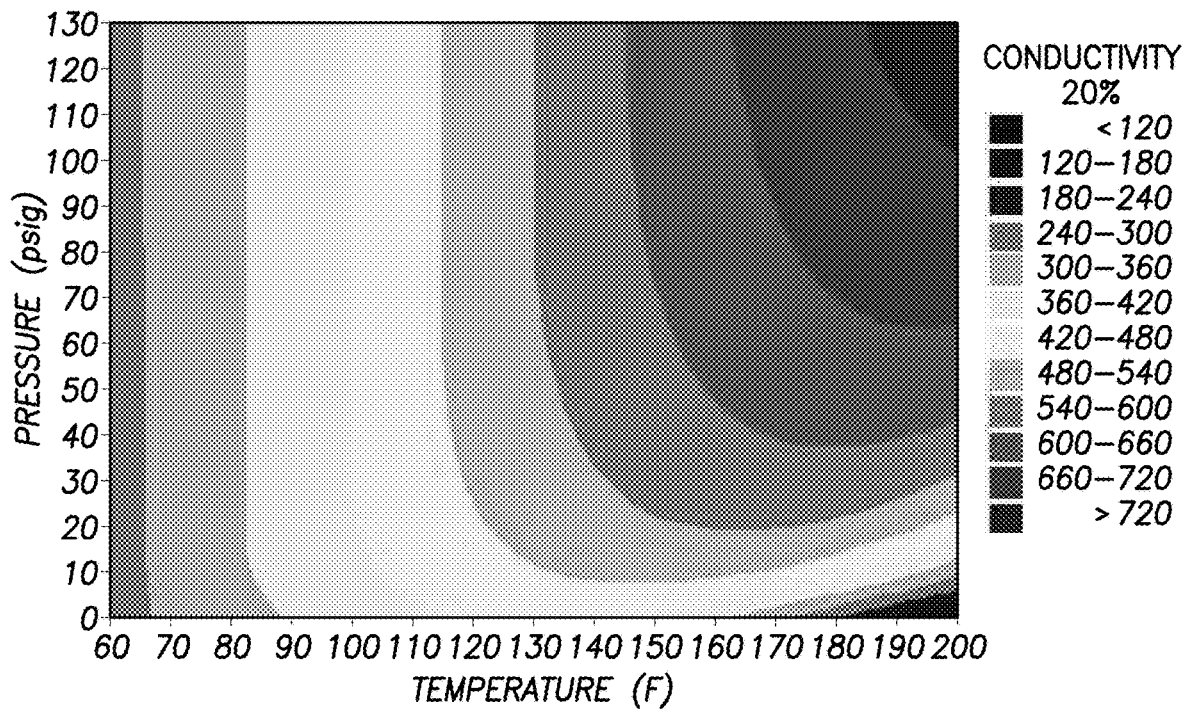
FIG. 5 illustrates a chart of temperature (° F.) versus pressure (psig) for electrolytic conductivity (mS/cm) of 20 wt % ammonium bisulfide.
Figure 6:
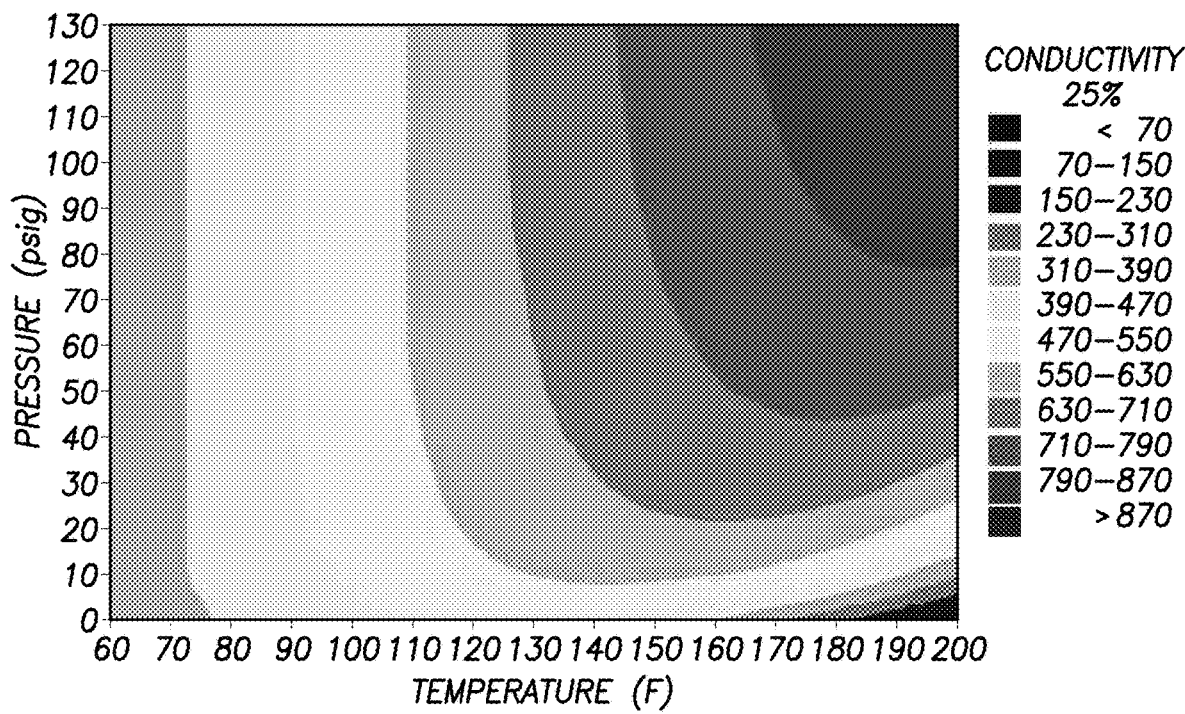
FIG. 6 illustrates a chart of temperature (° F.) versus pressure (psig) for electrolytic conductivity (mS/cm) of 25 wt % ammonium bisulfide.
Figure 7:
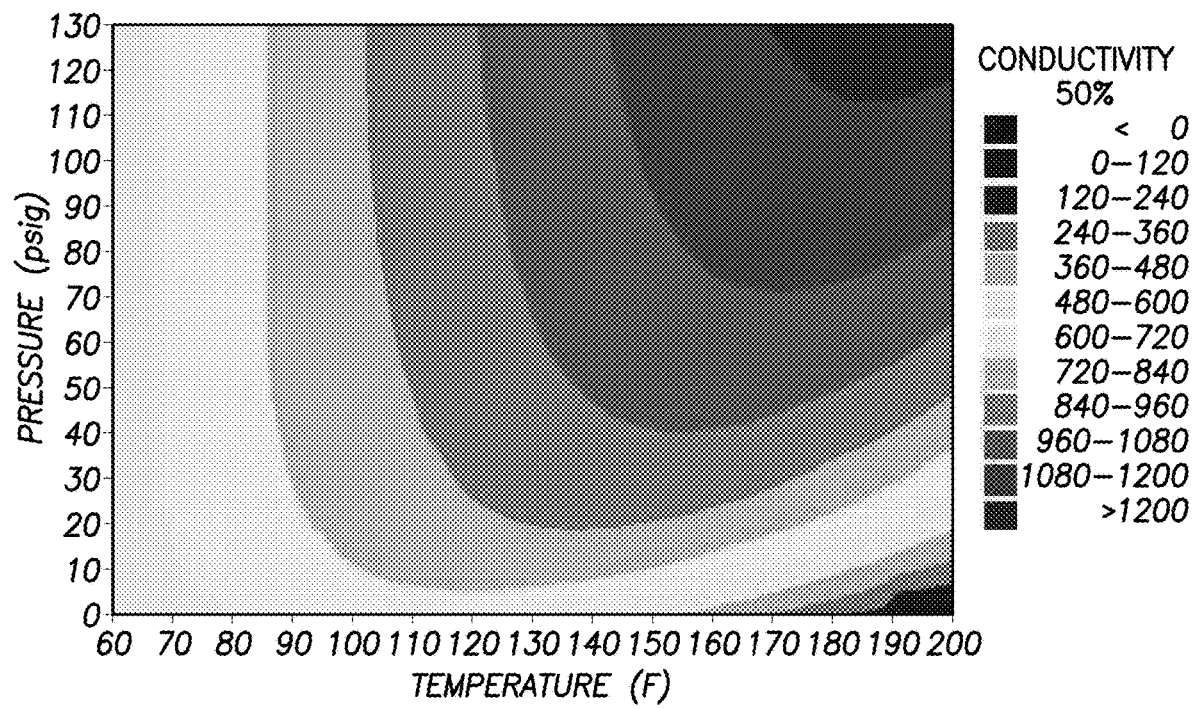
FIG. 7 illustrates a chart of temperature (° F.) versus pressure (psig) for electrolytic conductivity (mS/cm) of 50 wt % ammonium bisulfide.
Figure 8:
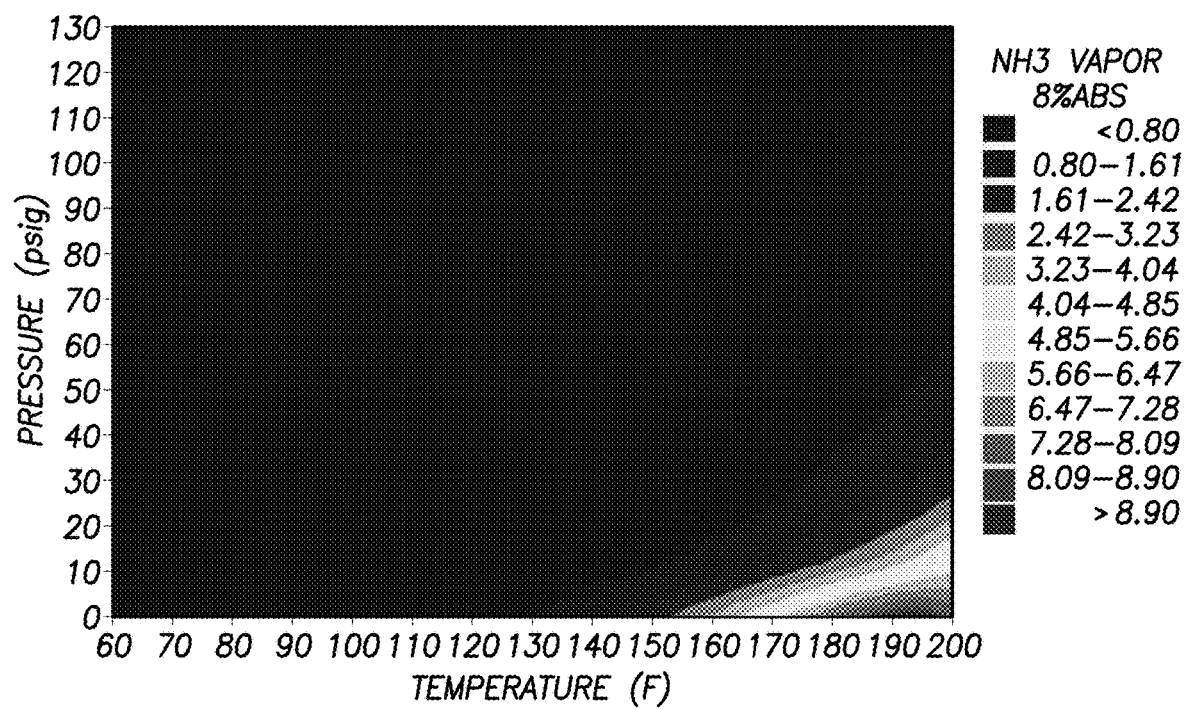
FIG. 8 illustrates a chart of temperature (° F.) versus pressure (psig) for ammonia in vapor phase (mass %) at 8 wt % ammonium bisulfide.
Figure 9:
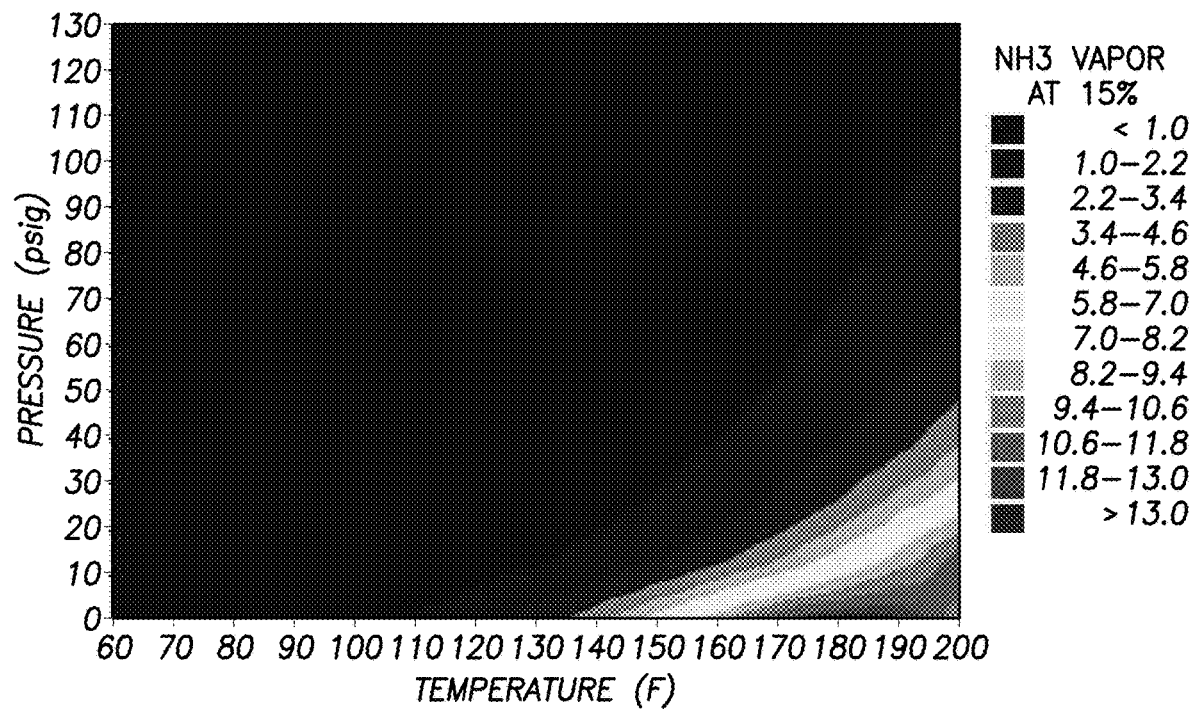
FIG. 9 illustrates a chart of temperature (° F.) versus pressure (psig) for ammonia in vapor phase (mass %) at 15 wt % ammonium bisulfide.
Figure 10:
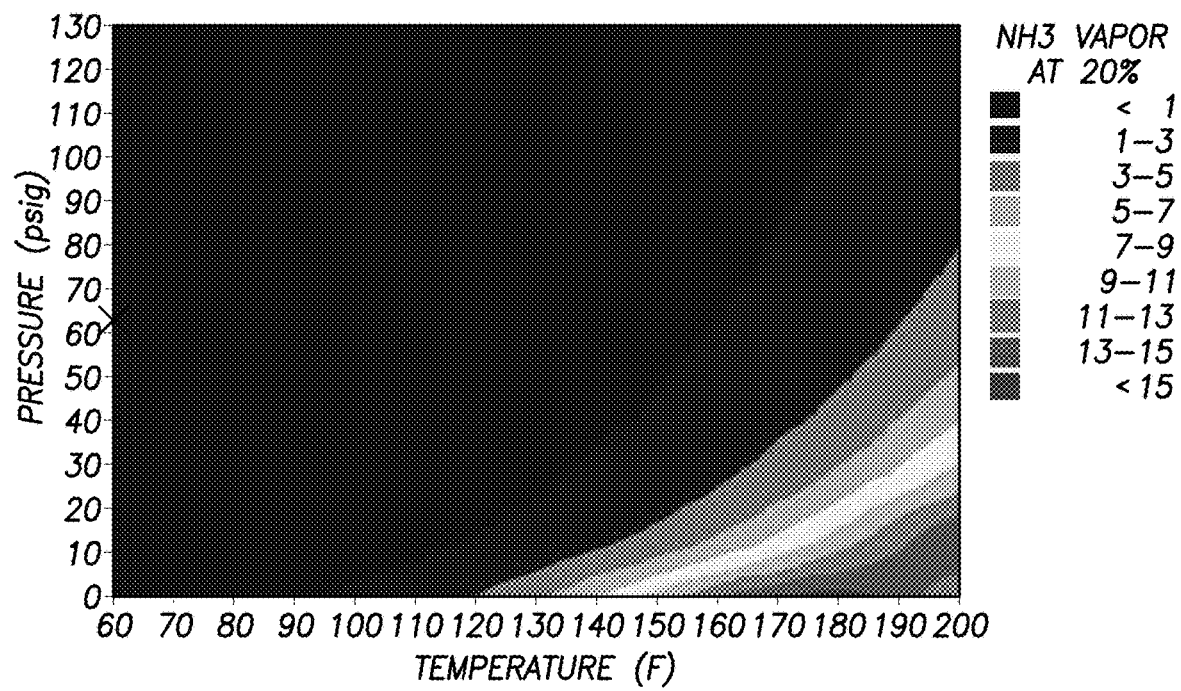
FIG. 10 illustrates a chart of temperature (° F.) versus pressure (psig) for ammonia in vapor phase (mass %) at 20 wt % ammonium bisulfide.
Figure 11:
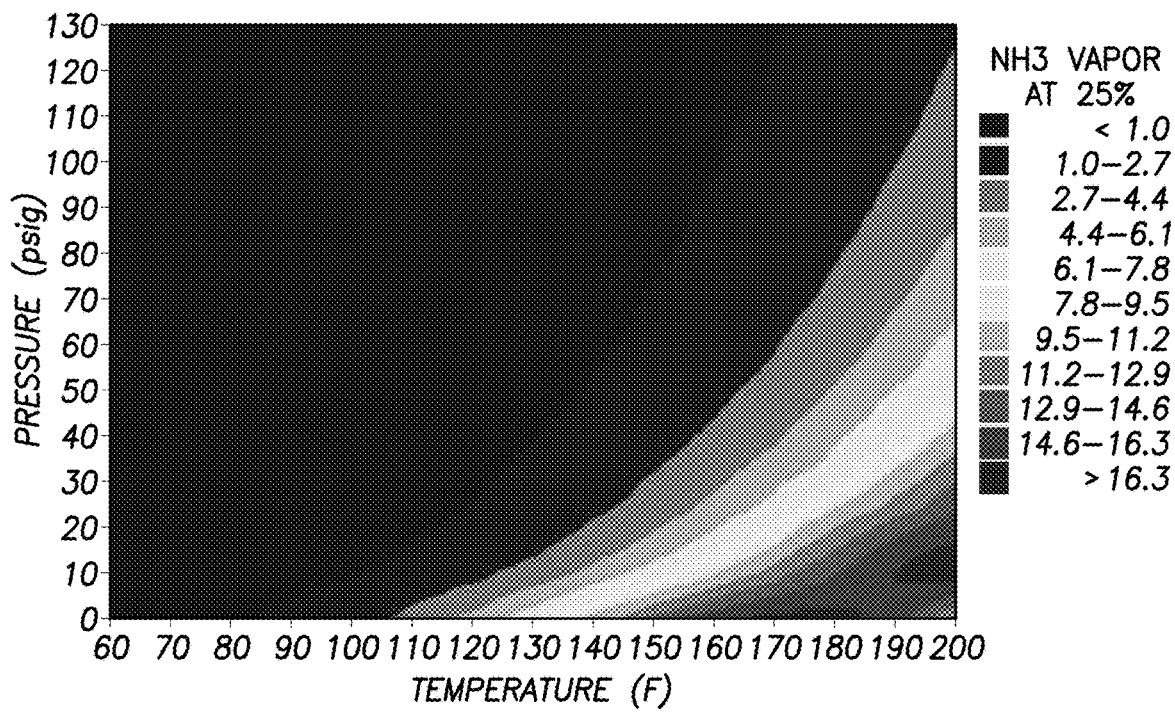
FIG. 11 illustrates a chart of temperature (° F.) versus pressure (psig) for ammonia in vapor phase (mass %) at 25 wt % ammonium bisulfide.
Figure 12:
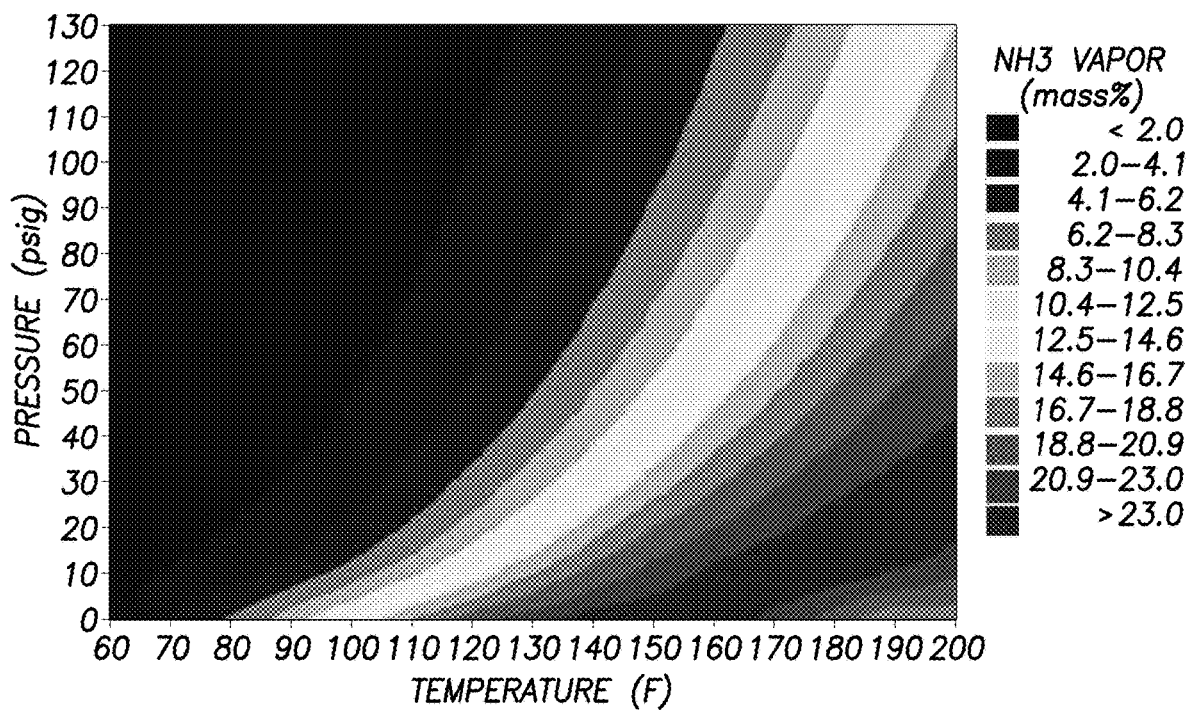
FIG. 12 illustrates a chart of temperature (° F.) versus pressure (psig) for ammonia in vapor phase (mass %) at 50 wt % ammonium bisulfide.
Figure 13:
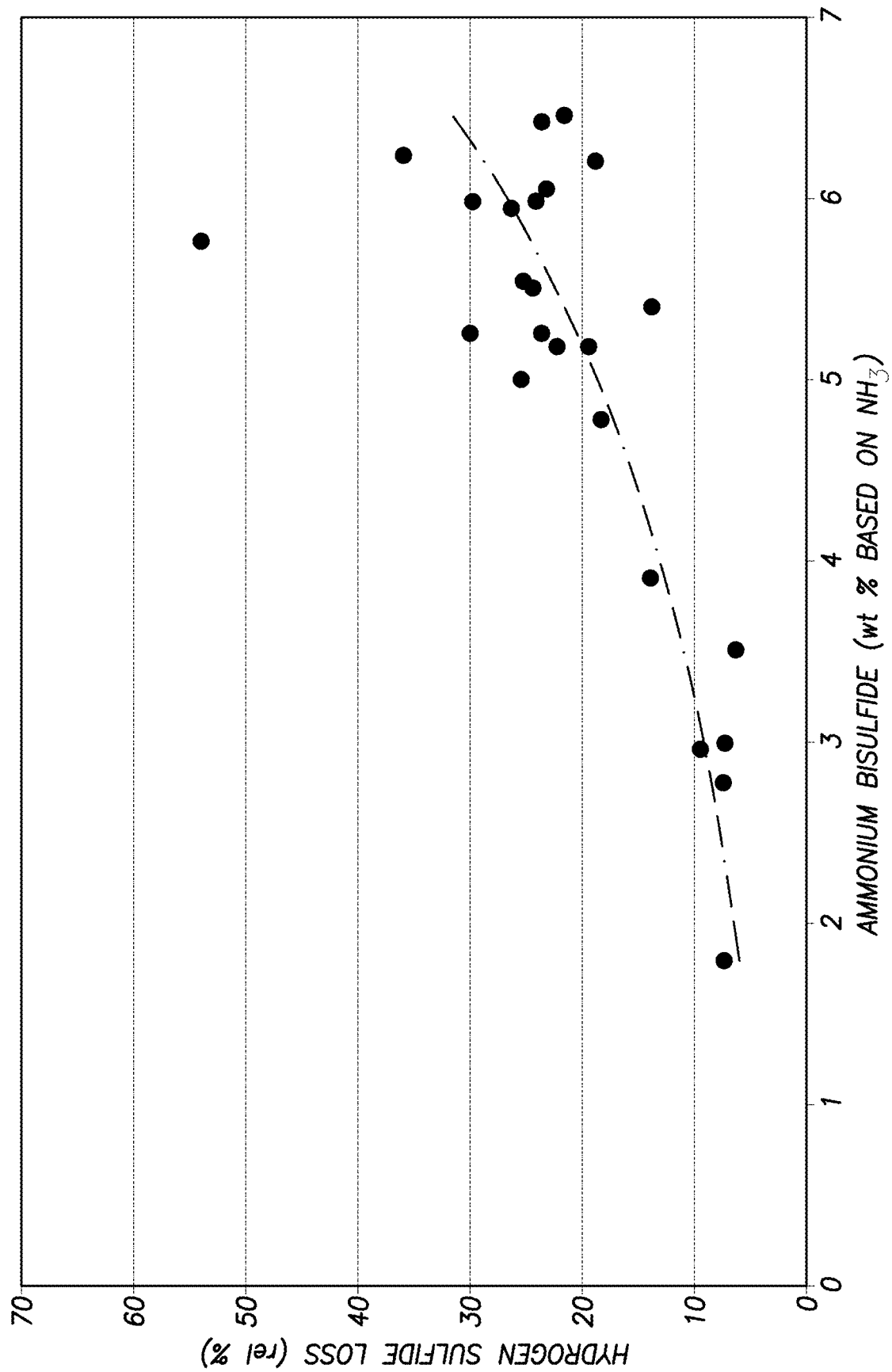
FIG. 13 illustrates a chart of ammonium bisulfide (wt % based on ammonia) versus hydrogen sulfide loss (rel %), showing a preferential loss of hydrogen sulfide relative to ammonia during atmospheric flash sampling of hydrotreater sour water.

FIG. 2 shows a flow chart for a method of measuring ammonium bisulfide concentration in a fluid stream. A first step 201 of the method includes measuring conductivity of the fluid stream. In an embodiment, the computing device 1700 of the analyzer 111 receives a first signal indicative of conductivity from the conductivity cell 110 for the fluid stream 102, as discussed above.

In a second step 202, the method includes measuring temperature of the fluid stream. In an embodiment, the temperature sensor 112 is inserted directly into the fluid stream 102, as discussed above. In an embodiment, the computing device 1700 receives a second signal indicative of temperature from the temperature sensor 112 for the fluid stream 102, as discussed above.

A calculation step 203 uses the temperature and the conductivity measured in the first and second steps 201, 202 for determining the ammonium bisulfide concentration based upon an ammonium bisulfide calibration algorithm or curve, as discussed further below. In an embodiment, the computing device 1700 determines the ammonium bisulfide concentration for the fluid stream 102 based on the measured temperature from the temperature sensor 112 for the stream 102 and the measured conductivity for the stream 102, wherein the measured temperature and measured conductivity are correlated to the calibration algorithm or curve to determine the ammonium bisulfide concentration for the stream 102. In an embodiment, the computing device 1700 determines the ammonium bisulfide concentration based on the first and second signals, wherein the first and second signals are correlated to the calibration algorithm or curve to determine the ammonium bisulfide concentration, as discussed below. The method further includes a user interface step 204 by outputting the ammonium bisulfide concentration determined in the calculation step 203 to the presentation component, such as a display.

In an embodiment, the method further includes a step of directing at least part of a sour water flow at a refinery to provide the fluid stream. At least part of a sour water flow from a hydrotreater may provide the fluid stream.

In an embodiment, the method further includes the step of outputting the ammonium bisulfide concentration to a presentation component, such as a display.

In an embodiment, the method includes the step of measuring pressure of the fluid stream. In an embodiment, the computing device 1700 receives a third signal indicative of pressure from the pressure sensor 114 for the fluid stream 102, as discussed above. In an embodiment, the computing device 1700 determines the ammonium bisulfide concentration based on the first, second and third signals, wherein the first, second and third signals are correlated to a calibration algorithm or curve to determine the ammonium bisulfide concentration, as discussed below.

In an embodiment, the method includes the step of filtering the fluid stream before measuring the electrolytic conductivity.

In an embodiment, the method includes the step of tagging the ammonium bisulfide concentration if flow rate of the fluid stream is below a threshold value.

Ammonium Bisulfide Calibration Model

Hydrotreater sour water is essentially a single salt solution of ammonium bisulfide as follows:

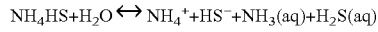

Thus, any bulk property of the solution may be used to quantify the ammonium bisulfide concentration. The present invention uses electrolytic conductivity to determine the concentration of the ammonium bisulfide salt. Because the ammonium bisulfide salt composition is relatively fixed, there is direct correlation between the salt concentration and the electrolytic conductivity.

Typically, such an analyzer would be calibrated by preparing solutions of various known salt concentrations and determining the electrolytic conductivity of such salt solutions. For an ammonium bisulfide analyzer, this calibration strategy is hindered by three problems:

1) an ammonium bisulfide salt is not commercially available;
2) ammonium bisulfide solutions are not stable under atmospheric conditions due to oxidation and degassing of hydrogen sulfide; and
3) ammonium bisulfide solutions are highly toxic due to the degassing of hydrogen sulfide.

Therefore, the traditional calibration procedure is not practical (or prudent) for the ammonium bisulfide analyzer. Instead, the present invention avoids these problems by implementing a "virtual" calibration procedure for the ammonium bisulfide analyzer. Alternatively, the invention avoids these problems by using a "proxy" calibration procedure for the ammonium bisulfide salt, as discussed further below.

The electrolytic conductivity of an ammonium bisulfide solution is a function of ammonium bisulfide salt concentration, temperature and pressure. Thus, the ammonium bisulfide calibration procedure requires at least two ammonium bisulfide relationships as follows:

1) an ammonium bisulfide salt concentration versus electrolytic conductivity relationship; and
2) an electrolytic conductivity versus temperature relationship; and
3) optionally, an electrolytic conductivity versus pressure relationship or, alternatively, a temperature versus pressure relationship for various ammonium bisulfide salt concentrations.

This calibration model may be developed by using an electrolytic solution modeling software to determine the ammonium bisulfide algorithm or curve, or by using a proxy solution for the ammonium bisulfide to determine the algorithm or curve. For example, a suitable electrolytic solution modeling software is available from OLI Systems, Inc.

In some embodiments, theoretical calculations enable defining the ammonium bisulfide calibration algorithm or calibration curve. The theoretical calculations may include several, such as 1000 or more, calculated values for the conductivity over potential operating temperatures, such as about 60 to about 140° F. (i.e., about 15 to about 60° C.), and a potential ammonium bisulfide concentration range, such as about 0 to about 50 weight percent (wt %). See FIGS. 3-7.

According to some embodiments, the calibration model assumes that the electrolytic conductivity of the ammonium bisulfide solution is not particularly dependent on pressure. The temperature-pressure conditions, where conductivity remains relatively constant with pressure, depend on the concentration of the ammonium bisulfide salt. See FIGS. 3-7 (left half). At any given concentration of the ammonium bisulfide salt, changes in pressure do not affect the electrolytic conductivity below a threshold temperature for that salt concentration. Id. For example, at a concentration of about 8 wt % ammonium bisulfide salt, changes in pressure do not affect the electrolytic conductivity below about 100° F. (i.e., about 38° C.). See FIG. 3. These calculated values showed near linear conductivity changes over the concentration range and enabled deriving the algorithm or curve for a concentration-conductivity function with a temperature compensation factor. See FIGS. 3-7.

As can be seen from FIGS. 3-7 (left half), lower-temperature, moderate-pressure conditions are highly favorable for performing online ammonium bisulfide analyses. The linear behavior of electrolytic conductivity under lower-temperature, moderate-pressure conditions make it relatively easy to develop accurate ammonium bisulfide calibration algorithms or curves. Id. For example, hydrotreater sour water temperatures of less than about 120° F. (i.e., about 50° C.) and pressures of between about 30 to about 200 psig (i.e., about 206 to about 1380 kilopascal) are ideal for the present invention. Importantly, these operating conditions are highly compatible with sour water streams produced in refinery hydroprocessing units.

For some embodiments, the calibration model assumes that the electrolytic conductivity of the ammonium bisulfide solution is not particularly dependent on pressure at temperatures above a threshold temperature. The temperature-pressure conditions, where conductivity remains relatively constant with pressure, depend on the concentration of the ammonium bisulfide salt and the temperature of the stream. See FIGS. 3-7 (right upper quadrant). At any given concentration of the ammonium bisulfide salt at temperatures above the threshold temperature, changes in pressure do not affect the electrolytic conductivity above a threshold pressure for that salt concentration. Id. As can be seen by FIGS. 3-7, the threshold pressure increases as the temperature increases. Id. For example, at a concentration of about 8 wt % ammonium bisulfide salt, changes in pressure do not affect the electrolytic conductivity above about 130° F. and about 20 psig (i.e., above about 54° C. and about 138 kilopascals), above about 160° F. and about 50 psig (i.e., 70° C. and about 345 kilopascals), and above about 190° F. and about 90 psig (i.e., above about 88° C. and about 620 kilopascals). See FIG. 3. These calculated values showed near linear conductivity changes over the concentration range and enabled deriving the ammonium bisulfide algorithm or curve for a concentration-conductivity function with a temperature compensation factor and a pressure compensation factor. See FIGS. 3-7.

As can be seen from FIGS. 3-7 (upper right quadrant), higher-temperature, moderate-to-higher-pressure conditions are moderately favorable for performing online ammonium bisulfide analyses. The near linear behavior of electrolytic conductivity under higher-temperature, higher-pressure conditions make it possible to develop reasonably accurate ammonium sulfide calibration algorithms or curves. Id.

As can be seen from FIGS. 3-7 (lower right quadrant), high-temperature, low-pressure conditions are not favorable for performing online ammonium bisulfide analyses. The non-linear behavior of electrolytic conductivity under high-temperature, low-pressure conditions make it extremely difficult to develop accurate ammonium bisulfide calibration algorithms or curves.

By way of explanation, the non-linear behavior of electrolytic conductivity illustrated in FIGS. 3-7 is due to the thermal decomposition of the ammonium bisulfide salt into ammonia gas and hydrogen sulfide gas. See FIGS. 8-12. Thus, as the ammonium bisulfide salt decomposes, the electrolytic conductivity of the salt solution decreases. Id. The amount of ammonia (and hydrogen sulfide) in the aqueous phase increases with increasing temperature, but it decreases with increasing pressure. Id. For measurements taken under high-temperature, low-pressure conditions where ammonia (and hydrogen sulfide) is present in the vapor phase, the error between the actual ammonium bisulfide salt concentration and the measured concentration is greater. The greater the amount of ammonia (and hydrogen sulfide) in the vapor phase; the larger the error in the measured concentration. As long as the analyzer operates under temperature and pressure conditions where the amount of ammonia in the vapor phase is less than about 1 to 2 wt %, a temperature compensation factor can be adjusted to produce an appropriate calibration curve.

Further, the error between the actual ammonium bisulfide salt concentration and the measured concentration can be reduced if a multi-point calibration curve is used. If the calibration curve is weighted on the higher end, the error can be further reduced. For example, for a hydrotreater sour water stream with a concentration of about 25 wt % ammonium bisulfide salt, a calibration curve of about 0 wt % ammonium bisulfide salt, about 10 wt %, about 15 wt %, about 20 wt % and about 25 wt % would reduce the error.

Laboratory Testing of Online Ammonium Bisulfide Analyzer

An online ammonium bisulfide analyzer 111 was fabricated to evaluate the calibration model calculations for standard (i.e., known concentration) proxy solutions of ammonium bicarbonate in a laboratory and to compare the online analyzer to refinery grab sampling and laboratory analysis methods in a refinery. The laboratory evaluations of the analyzer 111 were conducted using a process water simulator. The process water simulator is a programmable flow loop system that circulates water solutions through an analyzer at different temperature, pressure and flow rate conditions. Data acquisition and control of the process water simulator was accomplished using a distributed control system (e.g., MicroMod Automation). Using the control system, the flow loop was programmed to step through a sequence of temperature, pressure and flow rate while continuously logging data from multiple sensors, such as an electrolytic conductivity cell 110, a temperature sensor 112, a pressure sensor 114, and a flow meter 116, located around the analyzer 111.

For the laboratory evaluations of the analyzer, ammonium bicarbonate was used as the conductive salt. Ammonium bicarbonate is a relatively good proxy for ammonium bisulfide because their acid-base and solution equilibrium are quite similar. The evaluations covered a range of process condition as follows:
1) about 70 to about 200° F. (i.e., about 21 to about 93° C.);
2) about 15 to about 45 psig (i.e., about 105 to about 310 kilopascals);
3) about 0 to about 10 wt % ammonium bicarbonate; and
4) about 0.1 to about 0.5 gallons per minute (gpm).

Because the experimental results had excellent agreement with the calibration model calculations in these proof-of-concept laboratory evaluations, the online analyzer 111 was shipped to the refinery for field testing.

Field Testing of Online Ammonium Bisulfide Analyzer

After the analyzer 111 was brought online at the refinery, the sensor readings, such as an electrolytic conductivity cell 110, a temperature sensor 112, a pressure sensor 114, and a flow meter 116, were updated and logged five times per minute. The data logged from the previous twenty-four hour period was compared to refinery grab sampling and laboratory analysis methods.

Comparison of Online Analyzer with Refinery Grab Sampling and Laboratory Analyses Most refineries use the following analytical methods to determine the concentration of ammonium bisulfide in hydrotreater sour water streams:
1) total sulfide [$HS^-+H_2S(aq)$];
2) total ammonia [$NH_4^++NH_3(aq)$]; and
3) total alkalinity [$HS^-+NH_3(aq)$].

Figure 14:
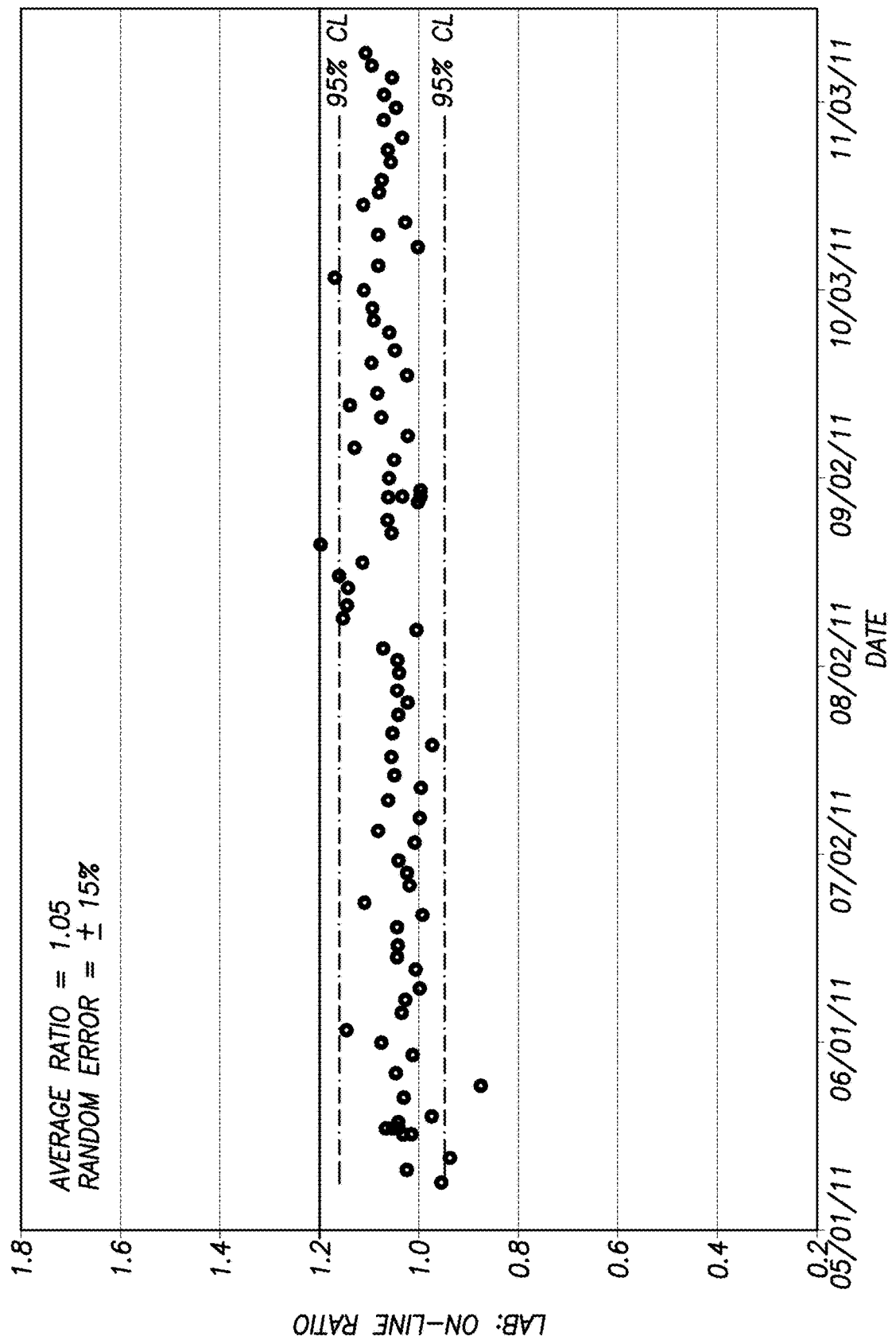
FIG. 14 illustrates a chart of date versus ratio of laboratory analysis (total alkalinity) to online analysis of ammonium bisulfide concentration.

Of these laboratory methods, total alkalinity and total ammonia are the most accurate. Total sulfide is the least accurate due to degassing of hydrogen sulfide during sample handling of grab samples. Sour water samples are collected by atmospherically flushing water into a sample bottle which results in a rapid depressurization of the sample. Because ammonia is not significantly lost during sampling, the total ammonia analysis yields more accurate results than the total sulfide analysis. See FIG. 14. As illustrated by FIG. 14, errors of about 30% are common when using the total sulfide analysis for determining ammonium bisulfide concentration.

FIG. 14 illustrates a comparison between laboratory analyses of grab samples and online results for the refinery unit. The grab samples were typically collected at about 02:00 on Monday, Wednesday and Friday. A laboratory determined the ammonium bisulfide concentration in the grab samples using an alkalinity titration method. The online results were calculated by averaging the analyzer readings between about 01:50 and 02:10 on Monday, Wednesday and Friday. On the average, the ammonium bisulfide concentration from the grab samples is about 5% higher than the online analyzer, as illustrated in FIG. 1. See FIG. 14. This offset is relatively small and likely due to the combined average biases for the two methods.

As illustrated by FIG. 14, however, there is a fair amount of scatter in the data. A linear regression of the laboratory analyses against the online analyzer results gives a coefficient of determination ($r^2$) of 0.85. The 0.85 coefficient indicates that the data contains 15% variation. This variation is likely due to sample handling errors in collecting the grab samples for the laboratory analyses. Thus, although the long-term averages for the laboratory analyses and the online analyzer results are within about 5% of one another, individual grab samples may have significant error.

Comparison of Online Analyzer with API Calculation Method

Some refineries use an American Petroleum Institute (API) calculation method to estimate ammonium bisulfide concentration. The API calculation requires the following key inputs:
1) nitrogen concretion in hydrotreater feed;
2) specific gravity of hydrotreater feed;
3) feed rate;
4) nitrogen concentration in hydrotreater product; and
5) water wash rate.

Figure 15:
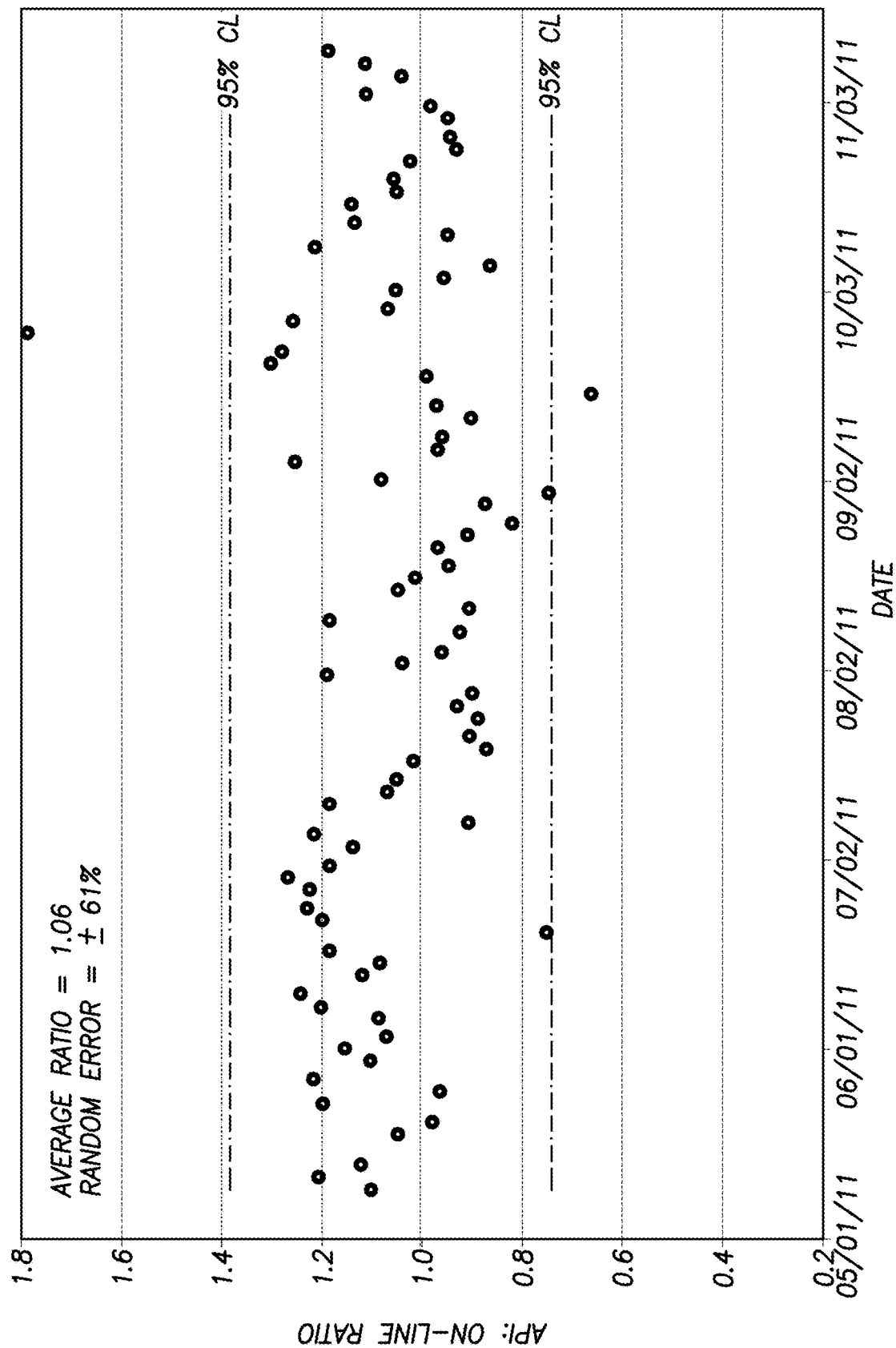
FIG. 15 illustrates a chart of date versus ratio of API calculation estimate to online analysis of ammonium bisulfide concentration.

FIG. 15 illustrates a comparison between the API calculation estimates and online results for the refinery unit. For the API calculation, the grab samples of the feed oil were typically collected on Monday, Wednesday and Friday. The hydrotreater product grab samples were collected every day. The nitrogen concentration in the oil feed and products samples were determined using a high temperature combustion method (Antek method). The oil feed rate and water wash rates were obtained by averaging the refinery's process variable data collected between 01:50 and 02:10 on Monday, Wednesday and Friday.

The API equation for estimating ammonium bisulfide (ABS) concentration is as follows:

$$ABS\ (wt\ \%) = 100 * ((OFR * 1000 * 350.49\ lb/barrel * OD)(FN-PN)/106) * (51.111\ g/mole\ ammonium\ bisulfide/14.0067\ g/mole\ nitrogen)/(W1+W2+W3) * 60\ min/hr * 24\ hr/day * 8.345\ lb/gallon\ of\ water$$

where
OFR=oil feed rate (MBPD);
OD=oil density (kg/L);
FN=feed nitrogen (ppm as nitrogen);
PN=product nitrogen (ppm as nitrogen);
W1=wash water rate (gpm);
W2=wash water rate (gpm); and
W3=water wash rate (gpm).

On the average, the ammonium bisulfide concentration from the API calculation estimate is about 6% higher than the online analyzer, as illustrated in FIG. 1. See FIG. 15. As illustrated by FIG. 15, the 95% confidence limits are much wider than the comparison shown in FIG. 14. A linear regression of the API calculated estimates against the online analyzer results yields a coefficient of determination ($r^2$) of 0.39. The 0.39 coefficient indicates that the data contains 61% variation. This variation is likely due to a combined effect of sampling, analysis and process variable errors. The largest errors are likely due to sample handling of and analytical problems with the feed oil. Although many refineries continuously receive a varying blend of feed oil streams such that the nitrogen concentration can vary significantly of short periods of time, the API calculation assumes a constant nitrogen concentration based upon the analytical results from the most recent grab sample. Further, the API calculation is further degraded by the combined errors of all the input data required for the estimate.

Therefore, the online results are within an acceptable range of both the laboratory-analyzed grab samples and/or the API calculated estimates.

The embodiments and examples set forth herein are presented to best explain the present invention and its practical application and to thereby enable those skilled in the art to make and utilize the invention. However, those skilled in the art will recognize that the foregoing description and examples have been presented for the purpose of illustration and example only. The description as set forth is not intended to be exhaustive or to limit the invention to the precise form disclosed. Many modifications and variations are possible in light of the above teaching without departing from the spirit and scope of the following claims. The invention is specifically intended to be as broad as the claims below and their equivalents.

DEFINITIONS

As used herein, the terms "a," "an," "the," and "said" means one or more, unless the context dictates otherwise.

As used herein, the term "about" means the stated value plus or minus a margin of error or plus or minus 10% if no method of measurement is indicated.

As used herein, the term "or" means "and/or" unless explicitly indicated to refer to alternatives only or if the alternatives are mutually exclusive.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "containing," "contains," and "contain" have the same open-ended meaning as "comprising," "comprises," and "comprise," provided above.

As used herein, the terms "having," "has," and "have" have the same open-ended meaning as "comprising," "comprises," and "comprise," provided above.

As used herein, the terms "including," "includes," and "include" have the same open-ended meaning as "comprising," "comprises," and "comprise," provided above.

As used herein, the phrase "consisting of" is a closed transition term used to transition from a subject recited before the term to one or more material elements recited after the term, where the material element or elements listed after the transition term are the only material elements that make up the subject.

As used herein, the term "simultaneously" means occurring at the same time or about the same time, including concurrently.

INCORPORATION BY REFERENCE

All patents and patent applications, articles, reports, and other documents cited herein are fully incorporated by reference to the extent they are not inconsistent with this invention.

The invention claimed is:

1. A method for determining an ammonium bisulfide concentration, the method comprising: measuring electrolytic conductivity of an aqueous liquid stream by utilizing a conductivity cell to obtain a first signal representing a conductivity measurement; measuring temperature of the aqueous liquid stream by utilizing a temperature sensor to obtain a second signal representing a temperature measurement, wherein the temperature sensor is inserted directly into the aqueous liquid stream; measuring pressure of the aqueous liquid stream by utilizing a pressure sensor to obtain a third signal representing a pressure measurement; and determining the ammonium bisulfide concentration in the aqueous liquid stream based on the temperature measurement, the conductivity measurement, and the pressure measurement, wherein an analyzer receives and correlates the first signal the second signal and the third signal to a calibration algorithm to determine the ammonium bisulfide concentration, wherein the calibration algorithm compensates for any effects of pressure, temperature, or both on the conductivity measurement.

2. The method of claim 1, further comprising directing at least part of a sour water flow at a refinery to provide the aqueous liquid stream.

3. The method of claim 1, further comprising directing at least part of a sour water flow from a hydrotreater to provide the aqueous liquid stream.

4. The method of claim 1, further comprising outputting the ammonium bisulfide concentration to a display.

5. The method of claim 1, wherein the measuring of the electrolytic conductivity is performed by an inductive conductivity cell that is isolated from direct contact with the aqueous liquid stream.

6. The method of claim 1, wherein the analyzer receives a fourth signal from a flow meter indicative of the flow rate of the aqueous liquid stream, wherein the analyzer indicates an error in the ammonium bisulfide concentration if the flow rate of the aqueous liquid stream is below a threshold value.

7. The method of claim 1, further comprising filtering the aqueous liquid stream before measuring the electrolytic conductivity.

* * * * *